(12) United States Patent
Makino et al.

(10) Patent No.: US 7,732,492 B2
(45) Date of Patent: Jun. 8, 2010

(54) NATEGLINIDE-CONTAINING PREPARATION

(75) Inventors: Chisato Makino, Kawasaki (JP); Erika Motomura, Kawasaki (JP); Kunikazu Suzuki, Kawasaki (JP); Takahiko Andou, Yokkaichi (JP); Nobutaka Ninomiya, Yokkaichi (JP); Akira Yabuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/349,225

(22) Filed: Feb. 8, 2006

(65) Prior Publication Data

US 2006/0127475 A1    Jun. 15, 2006

(30) Foreign Application Priority Data

Aug. 8, 2003    (JP) ............................. 2003-290464

(51) Int. Cl.
    *A61K 31/13*    (2006.01)
    *A61K 31/70*    (2006.01)
    *A61P 3/10*     (2006.01)

(52) U.S. Cl. ..................... 514/641; 514/23; 562/433; 562/450

(58) Field of Classification Search ................ 424/486, 424/488, 464
    See application file for complete search history.

(56) References Cited

U.S. PATENT DOCUMENTS

| | | | |
|---|---|---|---|
| 3,931,404 A | | 1/1976 | Fulberth et al. |
| 4,017,598 A | * | 4/1977 | Ohno et al. ................ 424/469 |
| 6,143,323 A | | 11/2000 | Yabuki et al. |
| 6,294,197 B1 | | 9/2001 | Wagner et al. |
| 6,296,872 B1 | | 10/2001 | Yabuki et al. |
| 6,423,341 B1 | | 7/2002 | Yamaguchi |
| 6,559,188 B1 | * | 5/2003 | Gatlin et al. ................ 514/641 |
| 6,641,841 B2 | | 11/2003 | Yabuki et al. |
| 6,830,759 B2 | | 12/2004 | Makino et al. |
| 6,844,008 B2 | | 1/2005 | Yabuki et al. |
| 7,022,339 B2 | | 4/2006 | Makino et al. |
| 2001/0010825 A1 | * | 8/2001 | Shimizu et al. ............. 424/465 |
| 2001/0053791 A1 | * | 12/2001 | Babcock et al. ............. 514/419 |
| 2004/0014815 A1 | | 1/2004 | Ninomiya et al. |
| 2004/0029968 A1 | | 2/2004 | Ninomiya et al. |
| 2004/0146563 A1 | | 7/2004 | Hirai et al. |
| 2006/0029669 A1 | | 2/2006 | Makino et al. |
| 2006/0127475 A1 | | 6/2006 | Chisato et al. |

FOREIGN PATENT DOCUMENTS

| | | |
|---|---|---|
| CN | 1557291 A | 12/2004 |
| EP | 1 319 409 A1 | 6/2003 |
| JP | 49-86526 | 8/1974 |
| JP | 53-044618 | 4/1978 |
| JP | 57-109715 | 8/1982 |
| JP | 4-15221 | 3/1992 |
| JP | 09-208468 | 8/1997 |
| JP | 10-298062 | 11/1998 |
| JP | 11-514001 | 11/1999 |
| JP | 2000-103731 | 4/2000 |
| JP | 2000-143551 | 5/2000 |
| JP | 2000-506540 | 5/2000 |
| JP | 2000-178184 | 6/2000 |
| JP | 2000-351732 | 12/2000 |
| JP | 2002-87960 | 3/2002 |
| JP | 2002-173428 | 6/2002 |
| JP | 2002-326925 | 11/2002 |
| JP | 2003-505509 | 2/2003 |
| JP | 2003-509457 | 3/2003 |
| JP | 2003-201256 | 7/2003 |
| JP | 2003-535895 | 12/2003 |
| JP | 2005-513036 | 5/2005 |
| JP | 2008-265459 | 11/2008 |
| JP | 2009-51852 | 3/2009 |
| WO | WO 87/05804 | * 10/1987 |
| WO | WO 97/31639 | 9/1997 |
| WO | WO 98/22105 | 5/1998 |
| WO | WO 01/21159 A3 | 3/2001 |
| WO | WO 01/47514 A1 | 7/2001 |
| WO | WO 01/47557 A1 | 7/2001 |
| WO | WO 01/97805 | 12/2001 |
| WO | WO 02/34254 A1 | 5/2002 |
| WO | WO 02/40010 A1 | 5/2002 |
| WO | 2005/013964 | 2/2005 |
| WO | WO 2005/094812 A1 | 10/2005 |

OTHER PUBLICATIONS

W. Xu et al, "Preparation and quality investigation of nateglinide dispersible tablets", *Academic Journal of Guangdong College of Pharmacy*, Mar. 2003, vol. 19, No. 1. pp. 2-6 (Database CAPLUS on STn/AN 2003:538703).

* cited by examiner

*Primary Examiner*—Daniel M Sullivan
*Assistant Examiner*—Yevegeny Valenrod
(74) *Attorney, Agent, or Firm*—Oblon, Spivak, McClelland, Maier & Neustadt, L.L.P.

(57) ABSTRACT

The present invention provides a small-sized preparation that is easy to take, containing 26% or more of nateglinide and 28% or more of at least one disintegrant selected from the group consisting of carmellose or salts thereof, sodium carboxymethyl starch, croscarmellose sodium, crospovidone, partly pregelatinized starch and low-substituted hydroxypropyl cellulose, based on the total mass of the preparation. The preparation of the present invention has high contents of nateglinide, which can be absorbed immediately to exhibit a hypoglycemic action.

15 Claims, 1 Drawing Sheet

NATEGLINIDE-CONTAINING PREPARATION

BACKGROUND OF THE INVENTION

The present invention relates to a pharmaceutical preparation containing as the active substance nateglinide which is known as a hypoglycemic agent.

It is known (as disclosed in Japanese Patent Examined Publication (JP Kokoku) No. 4-15221) that nateglinide (chemical name: N-(trans-4-isopropylcyclohexanecarbonyl)-D-phenylalanine, which will be hereinafter referred to as "nateglinide") shows excellent hypoglycemic action when orally administrated and is useful as an agent for the treatment of diabetes.

Nateglinide has the excellent properties of controlling postprandial hyperglycemia, and tablets containing 30, 60, 90, 120 or 180 mg of nateglinide per tablet are clinically used in practice. The tablets containing 60, 90, 120 or 180 mg of nateglinide per tablet are advantageous in that a relatively large amount of active substance can be ingested in a single administration. However, with respect to the current pharmaceutical preparations containing an optimum dose (90 mg) of nateglinide, for example, in the form of concave shaped tablet (i.e., round-shaped tablet), 25 mass % of nateglinide and 30 mass % of hydroxypropyl cellulose with a low substitution degree as a disintegrant are contained based on the total mass of the preparation, and the tablet is designed to have a diameter of about 10.1 mm, a thickness of about 5.2 mm and a mass of 366 mg. In light of this, there is a need for a smaller-sized nateglinide-containing pharmaceutical preparation that is easier to take (for example, refer to WO98/22105, WO01/21159, WO01/47557, WO02/34254 and WO02/40010).

DISCLOSURE OF INVENTION

An object of the present invention is to provide a tablet composition that is easier to be taken while maintaining the original properties of nateglinide, i.e., rapid absorption without being influenced by meal to express the hypoglycemic action, which does not last for a long time.

The present invention relates to a pharmaceutical preparation for oral administration containing nateglinide as an active ingredient, wherein the nateglinide is contained in an amount of 26 mass % or more based on the total mass of the preparation and at least one disintegrant selected from the group consisting of carmellose or salts thereof, sodium carboxymethyl starch, croscarmellose sodium, crospovidone, partly pregelatinized starch and low-substituted hydroxypropyl cellulose is contained, and the total amount of the disintegrant is 28 mass % or more based on the total mass of the preparation.

Also, the present invention relates to the preparation comprising carmellose and/or crospovidone as the disintegrant.

Further, the present invention relates to the preparation comprising a mixture of carmellose and crospovidone as the disintegrant wherein the total amount of the disintegrant is 28 mass % or more based on the total mass of the preparation.

The present invention also relates to the preparation comprising a mixture of carmellose and crospovidone as the disintegrant wherein the total amount of the disintegrant is 33 mass % or more based on the total mass of the preparation.

Furthermore, the present invention relates to a preparation comprising 26 mass % or more of nateglinide, 28 mass % or more of the disintegrant, and in addition, an acidifying agent.

The present invention also relates to the preparation comprising 26 mass % or more of nateglinide, 28 mass % or more of the disintegrant, the acidifying agent, and in addition a moistening agent.

By designing the above-mentioned formulation for the tablet composition, the nateglinide-containing preparation (in the form of a tablet) can be made smaller in size, while maintaining the properties of nateglinide that can reduce postprandial increase in blood glucose level.

BEST MODE FOR CARRYING OUT THE INVENTION

Figure 1:
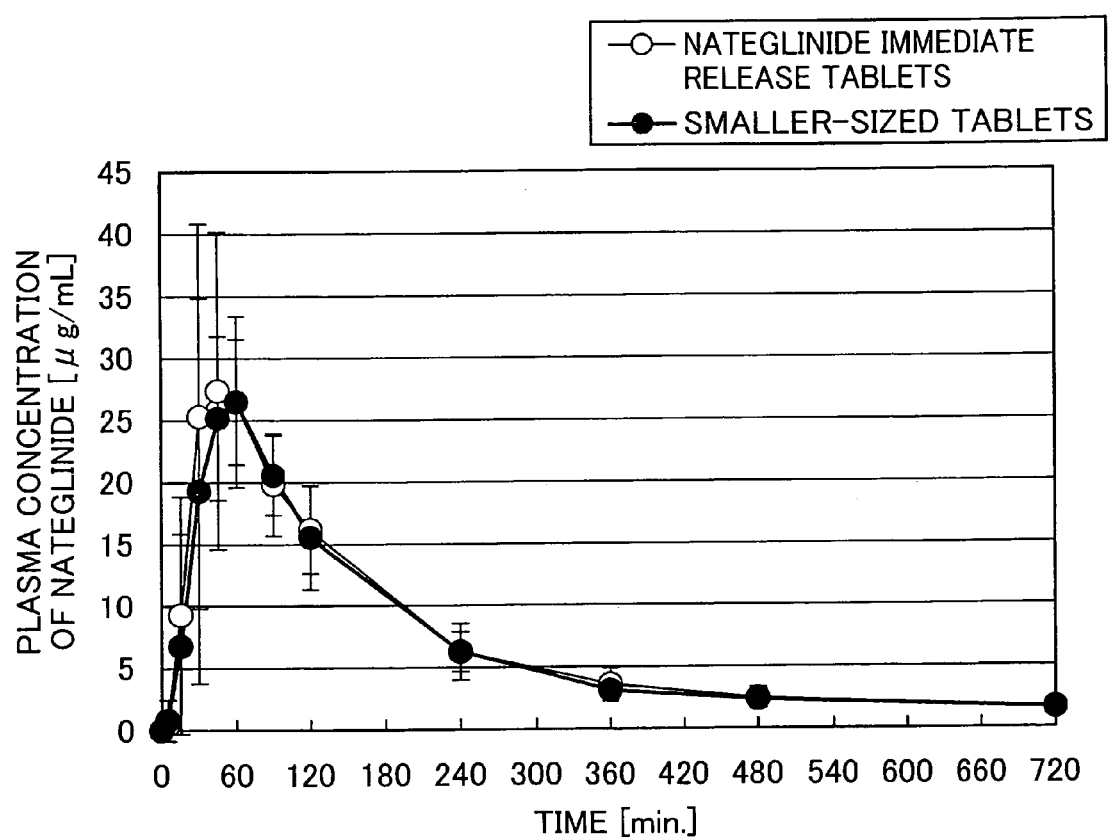
FIG. 1 is a graph which shows changes in concentration of nateglinide in the 5 blood plasma when a tablet obtained in Example 16 and a nateglinide-containing immediate release preparation are administered to dogs.

The active substance used as a hypoglycemic agent in the preparation of the present invention is nateglinide.

The method for preparing nateglinide is described, for example, as in JP Kokoku No. 4-15221 and the like. It is also known that nateglinide has crystal forms B, H and the like (Japanese Patent No. 2508949). The crystal form H is preferably used from the viewpoint of stability, although any of crystalline and amorphous forms are available with no difficulty so long as a smaller-sized preparation can be realized.

It is essential that the content of nateglinide in the preparation of the present invention be 26 mass % or more, preferably 26 to 60 mass %, more preferably 30 to 55 mass %, and further preferably 40 to 55 mass %, in order to obtain a preparation, particularly in the form of tablets. When the content of nateglinide is within the above-mentioned range, a tablet that is easy to hold and take can be advantageously obtained.

The disintegrant used in the present invention is at least one of carmellose or salts thereof, sodium carboxymethyl starch, croscarmellose sodium, crospovidone, low-substituted hydroxypropyl cellulose, or partly pregelatinized starch. Those may be used alone or in combination. Preferably, at least two or more disintegrants may be used in combination to achieve the object of the present invention. The combination of disintegrants is not particularly limited so long as the object of the present invention can be achieved. However, the combination of carmellose and crospovidone makes it possible to produce a smaller-sized preparation that contains high levels of nateglinide and shows particularly preferable dissolution properties and stability. To produce a preparation containing high contents (26 mass % or more) of nateglinide to control the postprandial elevated blood glucose level, which is a target of the present invention, it is necessary that the above-mentioned disintegrants be contained in an amount of 28 mass % or more in total, based on the total mass of the preparation. When the content of nateglinide is increased, for example, to 50 mass %, the content of disintegrant(s) may preferably be 35 mass % or more. The salts of carmellose include calcium, magnesium, potassium salts and the like. Of those disintegrants preferably used are carmellose, crospovidone, sodium carboxymethyl starch, carmellose calcium, and carmellose potassium. In particular, carmellose and/or crospovidone is preferable. Carmellose advantageously works to ensure excellent dissolution properties of nateglinide preparation throughout the physiological pH range, while crospovidone is preferable in ensuring excellent preservation stability of nateglinide preparation. When two or more disintegrants are used in combination, there is no particular limitation in the mixing ratio thereof so long as the object of the present invention can be attained. For example, when carmellose is used in combination with crospovidone, the ratio by mass of carmellose to crospovidone is preferably in the range of 1:2 to 2:1, more preferably in the range of 1:1.2 to 1.2:1. When the mixing ratio by mass of carmellose to crospovidone is within the above-mentioned range, excellent dissolution properties and preservation stability of nateglinide preparation can preferably be ensured. One preferable example showing the contents of nateglinide and disintegrant(s) is a formulation having 51% of nateglinide, 22% of carmellose and 19% of crospovidone. It is desirable to adjust the contents of the respective components in the above-mentioned manner because excellent dissolution properties and preservation stability of nateglinide preparation can be ensured.

The low-substituted hydroxypropyl cellulose that can be used as a disintegrant in the preparation of the present invention is a hydroxypropyl ether of cellulose where a limited part of hydroxyl group on the pyranose ring of cellulose is etherified with propylene oxide. The low-substituted hydroxypropyl cellulose is regarded as a compound having 5.0 to 16.0 mass % of hydroxypropoxyl group when determined on a dry basis (refer to the Japanese Pharmacopoeia 13th Edition D-885 to D-888 and the United States Pharmacopoeia 23rd Edition, pages 2253 to 2254). Examples of the low-substituted hydroxypropyl cellulose are low-substituted hydroxypropyl cellulose products, L-HPC (LH-11, LH-20, LH-21, LH-22, LH-30, LH-31 and LH-32) made by Shin-Etsu Chemical Co., Ltd., and so on.

The preparation of the present invention may further comprise an acidifying agent in addition to the above-mentioned ingredients. The acidifying agent includes organic acids and the like. In particular, glutamic acid hydrochloride, citric acid, ascorbic acid, and tartaric acid are preferable, and citric acid and glutamic acid hydrochloride are especially preferable. Those may be used alone or in combination. The acidifying agent may preferably be contained in an amount of 5% or more, more preferably 5 to 20%, based on the total mass of the preparation of the present invention. When the content of the acidifying agent to be added is within the above-mentioned range, immediate release performance of nateglinide can preferably be ensured. When the preparation of the present invention includes an acidifying agent, it is desirable to use an acidifying agent that may preferably show pH3 or less, more preferably pH1.5 to pH2.5, when 1 g of the acidifying agent is dissolved in 100 ml of purified water.

The preparation of the present invention may further comprise a moistening agent in addition to the above-mentioned composition. The moistening agent includes surfactants and inorganic salts. In particular, anhydrous silicon dioxide is preferable. The moistening agent may preferably be contained in an amount of 1% or more, more preferably 5 to 20%, based on the total mass of the preparation of the present invention. When the moistening agent is contained in such an amount as mentioned above, immediate release performance of nateglinide can preferably be ensured.

In addition to the above-mentioned essential ingredients, the tablet composition according to the present invention may further comprise as an excipient lactose, starch, crystalline cellulose, calcium hydrogen phosphate, light anhydrous silicic acid, titanium oxide, and magnesium aluminometasilicate. Of those excipients, lactose is preferable because lactose does not easily cause a change upon mixing with the compound (1). The content of the excipient may be within the range of 0 to 72 mass %, preferably 20 to 70 mass %, and further preferably 30 to 60 mass %.

Furthermore, hydroxypropyl cellulose is preferably blended as a binder in an amount of 0.1 to 5 mass %, preferably 0.5 to 4 mass % to facilitate the step of granulation in the production process. The hydroxypropyl cellulose used as the binder, which is discriminated from the previously mentioned low-substituted hydroxypropyl cellulose is regarded as a compound having 53.4 to 77.5 mass % of hydroxypropoxyl group when determined on a dry basis (refer to the Japanese Pharmacopoeia 13th Edition D-880 to D-885 and the United States Pharmacopoeia 23rd Edition page 2253). This type of hydroxypropyl cellulose is available as a commercial product of hydroxypropyl cellulose, HPC-L, HPC-L (fine powder type) or the like, made by Nippon Soda Co., Ltd.

The tablet composition according to the present invention may further comprise various additives conventionally used for the tablet compositions so long as the effects of the present invention will not be impaired. Examples of the additives include excipients such as crystalline cellulose, calcium hydrogen phosphate, starch, light anhydrous silicic acid, titanium oxide, magnesium aluminometasilicate, polyethylene glycol, sugars (e.g., lactose and mannitol) and the like; disintegrants such as starch, crystalline cellulose, hydroxypropyl starch and the like; binders such as gelatin, gum arabic, ethyl cellulose, polyvinyl alcohol and the like; lubricants such as stearic acid, magnesium stearate, calcium stearate, talc, hardened oil and the like; coating agents such as hydroxypropyl methyl cellulose, hydroxypropyl cellulose, methyl cellulose, ethyl cellulose, hydroxypropyl methyl cellulose phthalate, polyvinyl acetal diethylamino acetate, aminoalkyl methacrylate copolymer, polyvinyl acetate phthalate, polyethylene glycol (e.g., macrogol) and the like; coloring agents such as tar dye, titanium oxide and the like; flavoring agents such as citric acid, adipic acid, ascorbic acid, menthol and the like; and surfactants such as monostearic acid, glycerol, polysorbates (e.g., polysorbate 60, polysorbate 65 and polysorbate 80), sodium lauryl sulfate, sucrose fatty acid ester and the like.

The preparation of the present invention may be manufactured by the general process of granulation. To be more specific, nateglinide and the previously mentioned disintegrant(s), and other additives if required are weighed so that the respective contents may fall within the scope of the present invention, and those components are sufficiently mixed. Thereafter, the mixture was made into granules using water, which may contain lower alcohols such as ethanol, isopropanol and the like, and the resultant granules are dried. The granules may be subjected to sizing when necessary, and then compressed in a tableting machine to give tablets. The obtained tablets may be covered with a coating if desired.

The thus produced nateglinide-containing tablet according to the present invention can be made smaller in size, while maintaining the effects of the conventionally known nateglinide-containing preparations, that is, the effects of rapid disintegration in the digestive tract and absorption in the blood after oral administration to control the postprandial increase of blood glucose level. For example, a concave-shaped tablet containing 90 mg of nateglinide can be designed to have a diameter of 7.5 to 8.5 mm, a thickness of 3.5 to 4.9 mm and a volume of 122 to 228 $mm^3$, which can realize still easier oral administration as compared with the conventional nateglinide-containing preparations. Preferably, the preparation of the present invention may have a total mass of 164 to 300 mg, more preferably 165 to 225 mg.

When the preparation of the present invention is made into tablets, it is preferable that nateglinide be contained in one tablet in an amount of 60 mg or more, particularly, 60 mg, 90 mg, 120 mg or 180 mg. The most preferable amount is 90 mg per tablet. The content of nateglinide per tablet may be 35 mass % or more, preferably 50 to 70 mass %, and more preferably 55 to 65 mass %. The total mass may be in the range of 100 to 250 mg, preferably 130 to 180 mg.

In particular, preferably used is a nateglinide-containing tablet containing 50 mass % or more of nateglinide and 30 mass % or more of one or more disintegrants selected from the group consisting of carmellose or salts thereof, sodium carboxymethyl starch, croscarmellose sodium, crospovidone, partly pregelatinized starch and low-substituted hydroxypropyl cellulose. The disintegrant may preferably include at least carmellose and crospovidone. Furthermore, it is preferable that the content of nateglinide per tablet be 60 mg or more and the total mass of the tablet be 100 to 250 mg. Most preferably, the content of nateglinide per tablet may be 90 mg and the total mass of the tablet may be in the range of 130 to 180 mg.

EXAMPLE 1

Using a stirrer, a suspension containing 49.3 mass % of nateglinide, 0.49 mass % of hydroxypropyl cellulose ("Hydroxypropyl cellulose L-type" made by Nippon Soda Co., Ltd. with a viscosity of 6.0 to 10.0 mPa·S), and 0.97 mass % of polysorbate 80 was prepared. After 400 g of the above-mentioned suspension was kneaded with 191.6 g of a powder mixture of crospovidone and light anhydrous silicic acid "AEROSIL 200" made by Nippon Aerosil Co., Ltd., with a ratio by mass of 41.1:6.8. Granulation was then carried out by extrusion and the treatment by a Marumerizer followed, so that granules were obtained. The granules were dried in a fluidized-bed dryer until the exhaust temperature reached 50° C. or more. The obtained granules were subjected to screening and the fractions corresponding to 500 to 1400 μm were collected, thereby obtaining a superdisintegrant-containing nateglinide immediate-release preparation (content of nateglinide: 50.6%, content of disintegrant of the present invention: 41%, total mass of preparation: 177.9 mg (including 90 mg of nateglinide)).

EXAMPLE 2

Table shows the evaluation results of the preparation obtained in Example 1 in terms of the dissolution properties. The dissolution properties were evaluated by the paddle method (50 rpm) in accordance with the Japanese Pharmacopoeia 14th Edition. Using 900 ml of three kinds of test solutions (JP1 solution containing 0.6 w/v % of polysorbate 80, a ¼ times diluted McI 1 vaine buffer solution with pH4.0 containing 0.6 w/v % of polysorbate 80, and JP2 solution), the dissolution rates after a lapse of 8 minutes were determined. It was confirmed that the dissolution rates of the preparation obtained in Example 1 were as high as 70% in the JP1 solution containing 0.6 w/v % of polysorbate 80; 72% in the ¼ times diluted McI 1 vaine buffer solution with pH4.0 containing 0.6 w/v % of polysorbate 80; and 68% in the JP2 solution. Accordingly, the oral absorption properties are considered to show such a sufficient value as to effectively control the postprandial blood glucose level.

EXAMPLE 3

Nateglinide (562.5 g) and low-substituted hydroxypropyl cellulose (450.0 g) were mixed in a high-speed mixer/granulator "Hi-Speed Mixer" (made by Fukae Kogyo Co., Ltd.). After the addition of 1035.0 g of an aqueous solution of hydroxypropyl cellulose (1.45 w/w %), the resultant mixture was subjected to granulation. Thereafter, the granules thus obtained were further subjected to wet-type sizing using "Speed Mill" (made by Okada Seiko Co., Ltd.) and dried using a fluidized-bed dryer (made by Freund Corporation). The obtained granules were subjected to screening using a screen of 850 μm and only the oversize fraction was subjected to dry-type sizing using "Speed Mill". The fraction passing through the screen and the dry-type sized fraction were mixed together to obtain a nateglinide granulated substance. The granulated substance thus obtained was mixed with 300.0 g of lactose and 150.0 g of glutamic acid hydrochloride, and in addition, with 22.5 g of magnesium stearate, thereby giving granules ready for tablet compression. Using a rotary tableting machine, the granules for tablet compression were formed into tablets having a diameter of 9 mm (14R3r) and a mass of 240 mg (containing 38% of nateglinide).

EXAMPLE 4

Hydroxypropyl methyl cellulose (80 g), macrogol 6000 (15.0 g) and talc (24.0 g) were dissolved and dispersed in purified water (676.0 g), while titanium oxide (5.0 g) was dispersed in purified water (200.0 g). Both liquids were mixed together to obtain a coating liquid.

Using a tablet film coating apparatus ("Hicoater", made by Freund Corporation), the coating liquid was sprayed on the tablets obtained in Example 3, so that coated tablets were obtained (coating amount: 1.55% based on the uncoated tablets). At this stage, the content of nateglinide was 38% with respect to the uncoated tablets, and 37% with respect to the coated tablets.

COMPARATIVE EXAMPLE 1

The nateglinide granulated substance obtained in Example 3 was mixed with lactose (450.0 g). The resultant mixture was further mixed with magnesium stearate (22.5 g), thereby obtaining granules ready for tablet compression. Using a rotary tableting machine, the granules for tablet compression were formed into tablets having a diameter of 9 mm (14R3r) and a mass of 240 mg. The tablets were subjected to film coating in the same manner as in Example 4, to produce the coated tablets. The content of nateglinide was 38% with respect to the uncoated tablets, and 37% with respect to the coated tablets.

EXAMPLE 5

The dissolution properties were evaluated based on the Notification No. 452 of Pharmaceutical Affairs Bureau of Ministry of Health, Labour and Welfare. By the paddle method (50 rpm) in accordance with the Japanese Pharmacopoeia, the dissolution rates (values after a lapse of 20 minutes) of the preparations obtained in Example 4 and Comparative Example 1 were determined, using 900 ml of three kinds of test solutions (JP1 solution containing 0.75 w/v % of polysorbate 80, a phosphate buffer solution with pH6.5, and a phosphate buffer solution with pH7.2). The dissolution rates of the preparations obtained in Example 4 and Comparative Example 1 were respectively found to be 86% and 86% in the JP1 solution containing 0.75 w/v % of polysorbate 80; 93% and 48% in the phosphate buffer solution with pH6.5; and 88% and 76% in the phosphate buffer solution with pH7.2. It was confirmed that the results indicate sufficient dissolution rates of the preparation obtained in Example 4. Accordingly, the oral absorption properties are considered to show such a sufficient value as to effectively control the postprandial blood glucose level. In contrast to this, the dissolution rate of the preparation obtained in Comparative Example 1 is not sufficient in the phosphate buffer solution with pH6.5, which is not considered to effectively control the postprandial blood glucose level.

EXAMPLE 6

Nateglinide (60.0 g), partly pregelatinized starch (7.2 g), carmellose (24.0 g), croscarmellose sodium (3.6 g) and low-substituted hydroxypropyl cellulose (24.0 g) were mixed together using a high-speed mixer/granulator. After the addition of 100.0 ml of water, the resultant mixture was subjected to granulation. After the granules thus obtained were dried, magnesium stearate (1.2 g) was added to the granules. Through the step of compression, the granules were formed into tablets containing 75 mg of nateglinide (50%) and 73.5 mg of the disintegrants of the present invention (49%).

EXAMPLE 7

Nateglinide (120.0 g), carmellose (88.36 g) and hydroxypropyl cellulose (6.55 g) were mixed together using a high-speed mixer/granulator "Hi-Speed Mixer Mini" (made by Fukae Kogyo Co., Ltd.). After the addition of water, the resultant mixture was subjected to granulation. The granules thus obtained were dried using a fluidized-bed dryer ("FL0-1" made by Freund Corporation), and then forcibly passed through a screen of 850 μm. To the granulated substance (196.25 g) thus obtained, magnesium stearate (2.99 g) was added and mixed in a V type mixer, and then the mixture was compressed to give tablets (with a tablet mass of 163.6 mg, containing 90 mg of nateglinide (55%) and 66.3 mg of the disintegrant of the present invention (40%)).

Hydroxypropyl methyl cellulose (80 g), macrogol 6000 (15.0 g) and talc (24.0 g) were dissolved and dispersed in purified water (600.0 g), while titanium oxide (5.0 g) was dispersed in purified water (276.0 g). Both liquids were mixed together to obtain a coating liquid.

Using a tablet film coating apparatus ("Hicoater", made by Freund Corporation), the coating liquid (46.9 g) was sprayed on the tablets (300 g) including diluent tablets so that the coating film amount reached 2.5 mg per tablet. The coated tablets were thus obtained.

EXAMPLE 8

Nateglinide (120 g), sodium carboxymethyl starch (66.5 g), mannitol (21.8 g) and hydroxypropyl cellulose (6.54 g) were mixed together using a high-speed mixer/granulator "Hi-Speed Mixer Mini" (made by Fukae Kogyo Co., Ltd.). After the addition of water, the resultant mixture was subjected to granulation. The granules thus obtained were dried using a fluidized-bed dryer ("FL0-1" made by Freund Corporation), and then forcibly passed through a screen of 850 μm. To the granulated substance (195.86 g) thus obtained, magnesium stearate (2.97 g) was added and mixed in a V type mixer, and then the mixture was compressed to give tablets (with a tablet mass of 163.6 mg, containing 90 mg of nateglinide (55%) and 49.9 mg of the disintegrant of the present invention (30%)).

Using a tablet film coating apparatus ("Hicoater", made by Freund Corporation), the coating liquid (46.9 g) prepared in the same manner as in Example 7 was sprayed on the tablets (300 g) including diluent tablets so that the coating film amount reached 2.5 mg per tablet. The coated tablets were thus obtained.

EXAMPLE 9

Nateglinide (120 g), croscarmellose sodium (86.18 g), sodium lauryl sulfate (2.18 g) and hydroxypropyl cellulose (6.55 g) were mixed together using a high-speed mixer/granulator "Hi-Speed Mixer Mini" (made by Fukae Kogyo Co., Ltd.). After the addition of water, the resultant mixture was subjected to granulation. The granules thus obtained were dried using a fluidized-bed dryer ("FL0-1" made by Freund Corporation), and then forcibly passed through a screen of 850 μm. To the granulated substance (183.58 g) thus obtained, magnesium stearate (2.80 g) was added and mixed in a V type mixer, and then the mixture was compressed to give tablets (with a tablet mass of 163.6 mg, containing 90 mg of nateglinide (55%) and 64.6 mg of the disintegrant of the present invention (39%)).

Using a tablet film coating apparatus ("Hicoater", made by Freund Corporation), the coating liquid (46.9 g) prepared in the same manner as in Example 7 was sprayed on the tablets (300 g) including diluent tablets so that the coating film amount reached 2.5 mg per tablet. The coated tablets were thus obtained.

COMPARATIVE EXAMPLE 2

Nateglinide (120 g), lactose (61.96 g), corn starch (26.62 g) and hydroxypropyl cellulose (6.54 g) were mixed together using a high-speed mixer/granulator "Hi-Speed Mixer Mini" (made by Fukae Kogyo Co., Ltd.). After the addition of water, the resultant mixture was subjected to granulation. The granules thus obtained were dried using a fluidized-bed dryer ("FL0-1" made by Freund Corporation), and then forcibly passed through a screen of 850 μm. To the granulated substance (178.53 g) thus obtained, magnesium stearate (2.72 g) was added and mixed in a V type mixer, and then the mixture was compressed to give tablets (with a tablet mass of 163.8 mg, containing 90 mg of nateglinide (55%) and 20.0 mg of the disintegrants (12%)).

Using a tablet film coating apparatus ("Hicoater", made by Freund Corporation), the coating liquid (46.9 g) prepared in the same manner as in Example 7 was sprayed on the tablets (300 g) including diluent tablets so that the coating film amount reached 2.5 mg per tablet. The coated tablets were thus obtained.

EXAMPLE 10

By the paddle method (50 rpm) in accordance with the Japanese Pharmacopoeia 14th Edition, the dissolution properties of the preparations produced in Examples 7 to 9 and Comparative Example 2 were evaluated to determined the dissolution rates (values after a lapse of 20 minutes), using 900 ml of three kinds of test solutions (JP1 solution containing 0.6 w/v % of polysorbate 80, a ¼ times diluted McIlvaine buffer solution with pH4.0 containing 0.5 w/v % of polysorbate 80, and JP2 solution).

The dissolution rates of the preparations obtained in Examples 7 to 9 and Comparative Example 2 were respectively found to be 78%, 69%, 65% and 1% in the JP1 solution containing 0.6 w/v % of polysorbate 80; 80%, 82%, 74% and 1% in the ¼ times diluted McIlvaine buffer solution with pH4.0 containing 0.5 w/v % of polysorbate 80; and 94%, 76%, 90% and 7% in the JP2 solution. The preparations obtained in Examples 7 to 9 were found to have sufficient dissolution rates. Accordingly, the oral absorption properties are considered to be sufficient to effectively control the postprandial blood glucose level. In contrast to this, the dissolution rates of the preparation obtained in Comparative Example 2 are not sufficient in any solutions, which is not considered to effectively control the postprandial blood glucose level.

EXAMPLE 11

Nateglinide (600.1 g), carmellose (220.9 g), crospovidone (220.9 g) and hydroxypropyl cellulose (32.73 g) were mixed using a high-speed mixer/granulator "Hi-Speed Mixer 10JD" (made by Fukae Kogyo Co., Ltd.). After the addition of water, the resultant mixture was subjected to granulation. The granules thus obtained were subjected to wet-type milling using a "New Speed Mill ND-10" (made by Okada Seiko Co., Ltd.) and then dried using a fluidized-bed dryer ("FL0-5" made by Freund Corporation). The obtained granules were subjected to screening using a screen of 850 μm. The oversized fraction was further milled and passed through the screen of 850 μm.

To the granulated substance (357.0 g) thus obtained, carmellose (11.39 g), magnesium stearate (9.49 g) and talc (1.9 g) were added and mixed in a V type mixer, and the resultant mixture was compressed to give tablets (with a tablet mass of 171.4 mg, containing 90 mg of nateglinide (52%) and 71.4 mg of the disintegrants of the present invention (42%)).

Hydroxypropyl methyl cellulose (80 g), macrogol 6000 (15.0 g) and talc (24.0 g) were dissolved and dispersed in purified water (600.0 g), while titanium oxide (5.0 g) was dispersed in purified water (276.0 g). Both liquids were mixed together to obtain a coating liquid.

Using a tablet film coating apparatus ("Hicoater Mini", made by Freund Corporation), the coating liquid (49.9 g) was sprayed on the above-mentioned tablets (287 g), so that coated tablets were obtained.

The dissolution properties of the obtained tablets were evaluated by the paddle method (50 rpm) in accordance with the Japanese Pharmacopoeia, to determine the dissolution rate (value after a lapse of 15 minutes (n=3)), using 900 ml of JP2 solution (pH6.8). The dissolution rate of 95.4% clearly demonstrated excellent dissolution properties. Accordingly, the oral absorption is considered to be sufficient to effectively control the postprandial blood glucose level.

EXAMPLE 12

Nateglinide (600.13 g), carmellose (220.95 g), crospovidone (220.9 g) and hydroxypropyl cellulose (32.73 g) were mixed using a high-speed mixer/granulator ("10JD type" made by Fukae Powtec Co., Ltd.). After the addition of water, the resultant mixture was subjected to granulation. The granules thus obtained were dried using a fluidized-bed dryer ("FL0-5" made by Freund Corporation) and then subjected to screening using a screen of 850 μm. The oversized fraction was milled using a "New Speed Mill ND-10" (made by Okada Seiko Co., Ltd.) and passed through the screen of 850 μm.

To the granulated substance (343.48 g) thus obtained, crospovidone (10.90 g), magnesium stearate (5.42 g) and talc (3.62 g) were added and mixed in a V type mixer, and the resultant mixture was compressed to give tablets (with a tablet mass of 170.5 mg, containing 90 mg of nateglinide (53%) and 71.4 mg of the disintegrants of the present invention (42%)).

Hydroxypropyl methyl cellulose (80 g), macrogol 6000 (15.0 g) and talc (24.0 g) were dissolved and dispersed in purified water (600.0 g), while titanium oxide (5.0 g) was dispersed in purified water (276.0 g). Both liquids were mixed together to obtain a coating liquid.

Using a tablet film coating apparatus ("Hicoater Mini", made by Freund Corporation), the coating liquid (93.8 g) was sprayed on a mixture of the above-mentioned tablets (272.9 g) and diluent tablets (27.3 g), so that coated tablets were obtained.

The dissolution properties of the obtained tablets were evaluated by the paddle method (50 rpm) in accordance with the Japanese Pharmacopoeia, to determine the dissolution rate (value after a lapse of 15 minutes (n=3)), using 900 ml of JP2 solution (pH6.8). The dissolution rate of 94.9% clearly demonstrated excellent dissolution properties. Accordingly, the oral absorption is considered to be sufficient to effectively control the postprandial blood glucose level.

EXAMPLE 13

Nateglinide (600.0 g), carmellose (140.78 g), crospovidone (140.79 g) and hydroxypropyl cellulose (27.68 g) were mixed and the resultant mixture was subjected to granulation with the addition of water in a high-speed mixer/granulator ("10JD type" made by Fukae Powtec Co., Ltd.). The granules thus obtained were dried using a fluidized-bed dryer ("FL0-5" made by Freund Corporation) and then subjected to screening using a screen of 850 μm. The oversized fraction was milled using a "New Speed Mill ND-10" (made by Okada Seiko Co., Ltd.) and passed through the screen of 850 μm.

To the granulated substance (200.02 g) thus obtained, carmellose (10.74 g) and magnesium stearate (3.23 g) were added and mixed in a V type mixer, and the resultant mixture was compressed to give tablets (with a tablet mass of 145.9 mg, containing 90 mg of nateglinide (62%) and 49.6 mg of the disintegrants of the present invention (34%)).

Hydroxypropyl methyl cellulose (80 g), macrogol 6000 (15.0 g) and talc (24.0 g) were dissolved and dispersed in purified water (600.0 g), while titanium oxide (5.0 g) was dispersed in purified water (276.0 g). Both liquids were mixed together to obtain a coating liquid.

Using a tablet film coating apparatus ("Hicoater Mini", made by Freund Corporation), the coating liquid (46.9 g) was sprayed on a mixture of the above-mentioned tablets (115.5 g) and diluent tablets (184.5 g), so that coated tablets were obtained.

The dissolution properties of the obtained tablets were evaluated by the paddle method (50 rpm) in accordance with the Japanese Pharmacopoeia, to determine the dissolution rate (value after a lapse of 15 minutes (n=3)), using 900 ml of JP2 solution (pH6.8). The dissolution rate of 94.9% clearly demonstrated excellent dissolution properties. Accordingly, the oral absorption is considered to be sufficient to effectively control the postprandial blood glucose level.

EXAMPLE 14

Nateglinide (11 kg), carmellose (4.05 kg), crospovidone (4.05 kg) and hydroxypropyl cellulose (610.0 g) were mixed and the resultant mixture was subjected to granulation with the addition of water in a high-speed mixer/granulator ("VG-200 type" made by Powrex Corporation.). The granules thus obtained were dried using a fluidized-bed dryer ("FD-T-4 type" made by Powrex Corporation) and subjected to screening using a screen of 850 μm. The oversized fraction was crushed using a crusher "New Speed Mill ND-10" (made by Okada Seiko Co., Ltd.). This procedure was repeated twice, thereby obtaining about 39 kg of granules.

Using a mixer ("Bohle Container Mixer LM20 type"), the obtained granules (4.5 kg) were mixed with carmellose (135.0 g), and further with magnesium stearate (112.5 g) and talc (22.5 g), and the resultant mixture was compressed to give tablets (with a tablet mass of 170.9 mg, containing 90 mg of nateglinide (53%) and 71.1 mg of the disintegrants of the present invention (42%)). The above-mentioned procedure was repeated seven times, so that about 33 kg of uncoated tablets was obtained.

Hydroxypropyl methyl cellulose (7.2 kg) and macrogol 6000 (1.35 kg) were dissolved and dispersed in purified water (54 kg), while titanium oxide (0.45 kg) and iron sesquioxide (45 g) were dispersed in purified water (24.84 kg). Both liquids were mixed together. Talc (0.49 kg) was added to the above-mentioned mixture liquid and dispersed therein.

Using a tablet film coating apparatus ("Aqua Coater F130 type", made by Freund Corporation), the coating liquid (11.5 kg) was sprayed on a mixture of the above-mentioned tablets (about 6 kg) and diluent tablets (about 54 kg), so that coated tablets were obtained.

The dissolution properties of the obtained tablets were evaluated by the paddle method (50 rpm) in accordance with the Japanese Pharmacopoeia, to determine the dissolution rate (value after a lapse of 15 minutes (n=3)), using 900 ml of JP2 solution (pH6.8). The dissolution rate of 93.5% clearly demonstrated excellent dissolution properties. Accordingly, the oral absorption is considered to be sufficient to effectively control the postprandial blood glucose level.

EXAMPLE 15

Hydroxypropyl methyl cellulose (1600 g), macrogol 6000 (300 g) and talc (240 g) were dissolved and dispersed in purified water (12 kg), while titanium oxide (100 g) and iron sesquioxide (7 g) were dispersed in purified water (5520 g). Both liquids were mixed together.

Using a tablet film coating apparatus ("Aqua Coater F130 type", made by Freund Corporation), the coating liquid (11.3 kg) was sprayed on a mixture of the tablets obtained in Example 14 (about 6 kg) and diluent tablets (about 54 kg), so that coated tablets were obtained.

EXAMPLE 16

Nateglinide (11 kg), carmellose (4.05 kg), crospovidone (4.05 kg) and hydroxypropyl cellulose (610.0 g) were mixed and the resultant mixture was subjected to granulation with the addition of water in a high-speed mixer/granulator ("VG-200 type" made by Powrex Corporation.). The granules thus obtained were dried using a fluidized-bed dryer ("FD-T-4" made by Powrex Corporation) and then subjected to screening using a screen of 850 μm. The oversized fraction was milled using a "New Speed Mill ND-10" (made by Okada Seiko Co., Ltd.). This procedure was repeated twice, thereby obtaining about 39 kg of granules.

Using a mixer ("Bohle Container Mixer LM20 type"), the obtained granules (4.5 kg) were mixed with carmellose (135.0 g), and further with magnesium stearate (112.5 g) and talc (22.5 g), and the resultant mixture was compressed to give tablets (with a tablet mass of 170.9 mg, containing 90 mg of nateglinide (53%) and 71.1 mg of the disintegrants of the present invention (42%)). The above-mentioned procedure was repeated seven times, so that about 33 kg of uncoated tablets was obtained.

Hydroxypropyl methyl cellulose (640 g), macrogol 6000 (120 g) and talc (192 g) were dissolved and dispersed in purified water (4800 g), while titanium oxide (10 g) and iron sesquioxide (0.7 g) were dispersed in purified water (552 g). The former liquid weighing 1438.3 g and the latter liquid weighing 562.7 g were mixed together.

Using a tablet film coating apparatus ("HCT-MINI", made by Freund Corporation), the coating liquid (69.5 g) was sprayed on the above-mentioned tablets (375 g), so that coated tablets were obtained.

The dissolution properties of the obtained tablets were evaluated by the paddle method (50 rpm) in accordance with the Japanese Pharmacopoeia, to determine the dissolution rate (value after a lapse of 15 minutes (n=3)), using 900 ml of JP2 solution (pH6.8). The dissolution rate of 100.5% clearly demonstrated excellent dissolution properties. Accordingly, the oral absorption is considered to be sufficient to effectively control the postprandial blood glucose level.

TEST EXAMPLE 1

The oral absorption performance was evaluated in dogs using the tablets obtained in Example 16 and nateglinide immediate release tablets (washout: one week, 2×2 crossover design (n=6), male beagles, administration during fasting). The above-mentioned nateglinide immediate release tablets contain 25% of nateglinide and 30% of low-substituted hydroxypropyl cellulose serving as a disintegrant, based on the total mass of the tablets.

The changes in concentration of nateglinide in the blood plasma are shown in FIG. 1. The evaluation results of the nateglinide immediate release tablets are as follows. $AUC_{0 \to 12hr}$ (by trapezoidal rule): 85.6 μg·hr/mL, Cmax: 32.7 μg/mL. Those of the tablets obtained in Example 16 are as follows. $AUC_{0 \to 12hr}$ (by trapezoidal rule): 81.3 μg·hr/mL, Cmax: 31.1 g/mL. Their bioavailabilities were found to be almost the same.

INDUSTRIAL APPLICABILITY

According to the present invention, a small-sized preparation that is easy to be taken can be provided, with the properties of nateglinide as the antidiabetic agent being fully ensured.

The invention claimed is:

1. A tablet comprising nateglinide, wherein the nateglinide is contained in an amount of 50 mass % or more based on the total mass of the tablet, and at least one disintegrant selected from the group consisting of carmellose or salts thereof, sodium carboxymethyl starch, croscarmellose sodium, crospovidone, partly pregelatinized starch and low-substituted hydroxypropyl cellulose is contained, wherein the total amount of the disintegrant is 35 mass % or more based on the total mass of the tablet.

2. The tablet of claim 1, wherein the tablet contains 60 mg or more of the nateglinide.

3. The tablet of claim 1, wherein the disintegrant is at least one selected from the group consisting of carmellose, crospovidone, sodium carboxymethyl starch, carmellose calcium, and carmellose potassium.

4. The tablet of claim 1, wherein the disintegrant is carmellose.

5. The tablet of claim 1, wherein the disintegrant is a mixture of carmellose and crospovidone.

6. The tablet of claim 1, further comprising an acidifying agent.

7. The tablet of claim 6, wherein the acidifying agent is contained in an amount of 5 mass % or more based on the total mass of the tablet.

8. The tablet of claim 7, further comprising a moistening agent.

9. The tablet of claim 8, wherein the moistening agent is a surfactant or anhydrous silicon dioxide.

10. The tablet of claim 1, comprising 51 mass % of the nateglinide, 22 mass % of carmellose as the disintegrant, and 19 mass % of crospovidone as the disintegrant, based on the total mass of the tablet.

11. The tablet of claim 1, wherein the disintegrant comprises at least carmellose and crospovidone.

12. The tablet of claim 2, wherein the total mass of said tablet is 100 to 250 mg.

13. The tablet of claim 2, wherein said tablet contains 90 mg of nateglinide and the total mass of said tablet is 130 to 180 mg.

14. The tablet of claim 1, wherein the disintegrant is crospovidone.

15. The tablet of claim 1, wherein nateglinide is contained in an amount of 50 to 70 mass % based on the total mass of the tablet.

* * * * *

UNITED STATES PATENT AND TRADEMARK OFFICE
CERTIFICATE OF CORRECTION

PATENT NO. : 7,732,492 B2
APPLICATION NO. : 11/349225
DATED : June 8, 2010
INVENTOR(S) : Makino et al.

Page 1 of 1

It is certified that error appears in the above-identified patent and that said Letters Patent is hereby corrected as shown below:

On the title page, Item (63), the Related U.S. Application Data information should read:

-- Related U.S. Application Data
(63) Continuation of application No. PCT/JP2004/011711,
   filed on August 9, 2004. --

Signed and Sealed this

Tenth Day of August, 2010

David J. Kappos
*Director of the United States Patent and Trademark Office*